US00PP18295P2

(12) United States Plant Patent
Eggleton

(10) Patent No.: US PP18,295 P2
(45) Date of Patent: Dec. 11, 2007

(54) *LAVANDULA* PLANT NAMED 'MULBERRY RUFFLES'

(50) Latin Name: *Lavandula stoechas*
Varietal Denomination: Mulberry Ruffles

(76) Inventor: Steven Eggleton, 3 Harris Rd, Wonga Park, Melbourne, Vic (AU), 3115

( * ) Notice: Subject to any disclaimer, the term of this patent is extended or adjusted under 35 U.S.C. 154(b) by 38 days.

(21) Appl. No.: 11/437,496

(22) Filed: May 18, 2006

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV ROM GTITM Computer Database 2006/04 Citation for 'Mulberry Ruffles'.*

* cited by examiner

*Primary Examiner*—Wendy C. Haas

(57) ABSTRACT

A new cultivar of *Lavandula* plant named 'MULBERRY RUFFLES' that is characterized by early and repeat flowering, dense plant habit, short peduncle length, and fragrant flower spikes with medium length dark-pink sterile bracts. In combination, these traits at 'MULBERRY RUFFLES' apart from all other existing varieties of *Lavandula* known to the inventor.

1 Drawing Sheet

Genus: *LAVANDULA*
Species: *stoechas.*
Denomination: 'MULBERRY RUFFLES'.

BACKGROUND OF THE INVENTION

The present invention relates to a new and distinct cultivar of lavender known botanically as *Lavandula stoechas* and hereinafter referred to by the cultivar name 'MULBERRY RUFFLES'.

The new *Lavandula* cultivar named 'MULBERRY RUFFLES' is one individual selection in the Australian lavender 'Ruffles Series' that resulted from a formal breeding program. The breeding program was established in November 2001 and conducted by the inventor, at the inventor's nursery in Victoria, Australia. The inventor, a specialist in the genus *Lavandula,* selected 'MULBERRY RUFFLES' in 2003. Selection was based on a combination of early and repeat flowering, dense plant habit, dark-pink sterile bract color, medium sterile bract length, and short peduncle length.

'MULBERRY RUFFLES' is a selection arising from the controlled cross-pollination of *Lavandula stoechas* 'Kew Red' (unpatented) as the female parent, and *Lavandula stoechas* 'Pukehou' (unpatented) as the male parent. Cross-pollination of the parent plants took place in Park Orchards, Victoria, Australia in November 2001. From this cross the F1 generation was raised in February 2002 and grown to flowering maturity in September 2002. At this stage the F1 generation was self-pollinated and the seed sown in February 2003. From these F2 seedlings a selection was made when the plants had grown to flowering stage in 140 mm. containers.

'MULBERRY RUFFLES' is a perennial suitable for use in container and in the landscape. Cultural requirements include full sun, adequate but not excess water, and well-draining soil. Mature height is 60 cm. and mature width is 70 cm. 'MULBERRY RUFFLES' exhibits early and repeat flowering, dense plant habit, scented green foliage, short peduncle length, and scented flower spikes with medium length sterile bracts that are dark-pink in color.

The traits that distinguish 'MULBERRY RUFFLES' from the female parent 'Kew Red' are sterile bract length, and plant habit. 'Kew Red' exhibits short sterile bract length, and very dense plant habit, whereas 'MULBERRY RUFFLES' exhibits longer sterile bracts, and less dense plant habit. The traits that distinguish 'MULBERRY RUFFLES' from the male parent 'Pukehou' are peduncle length, plant habit, and sterile bract color. 'Pukehou' exhibits long peduncle length, medium to sparse plant habit, and purple sterile bract color, compared to 'MULBERRY RUFFLES' that exhibits short peduncle length, dense plant habit, and sterile bracts that are dark-pink in color.

The new *Lavandula* cultivar, named 'MULBERRY RUFFLES' was first asexually propagated by the inventor in 2004. Asexual propagation was accomplished at the inventor's nursery in Australia, and the method utilized was tip cuttings. Since that time 'MULBERRY RUFFLES' has been determined stable, and reproduces true to type in successive generations of asexual propagation.

SUMMARY OF THE INVENTION

The following traits have been repeatedly observed and represent the distinguishing characteristics of the new *Lavandula* cultivar named 'MULBERRY RUFFLES'. These traits in combination distinguish 'MULBERRY RUFFLES' from all other existing varieties of *Lavandula* known to the inventor. 'MULBERRY RUFFLES' has not been tested under all possible conditions and phenotypic differences may be observed with variations in environmental, climatic, and cultural conditions, without however, any variance in genotype.

1. 'MULBERRY RUFFLES' exhibits dense plant habit.
2. 'MULBERRY RUFFLES' exhibits scented flower spikes with sterile bracts that are medium in length and dark-ink in color.

3. 'MULBERRY RUFFLES' exhibits repeat flowering.
4. 'MULBERRY RUFFLES' exhibits fragrant green foliage.
5. 'MULBERRY RUFFLES' is one selection in the Australian lavender 'Ruffles Series' that blooms an average of two weeks earlier than many lavenders in commerce.
6. Cultural requirements for 'MULBERRY RUFFLES' are full sun, adequate but not excess water and well-draining soil.
7. 'MULBERRY RUFFLES' exhibits short peduncle length.
8. 'MULBERRY RUFFLES' is 60 cm in height and 70 cm. in width at maturity.
9. 'MULBERRY RUFFLES' is asexually propagated utilizing the method of tip and stem cuttings.
10. 'MULBERRY RUFFLES' is suitable for use as an ornamental plant in container or in the landscape.
11. 'MULBERRY RUFFLES' is hardy to USDA Zone 8.

BRIEF DESCRIPTION OF THE DRAWING

The accompanying drawing illustrates the overall appearance of the new *Lavandula* cultivar named 'MULBERRY RUFFLES' showing the colors as true as it is reasonably possible to obtain in color reproductions of this type. Color in the drawing may differ from the color values cited in the detailed botanical description, which accurately describe the actual color of the new *Lavandula* variety named 'MULBERRY RUFFLES'. The drawing was made of 9-month-old plants greenhouse grown in 16 cm. containers.

The drawing labeled

BOTANICAL DESCRIPTION OF THE PLANT

Figure 1:
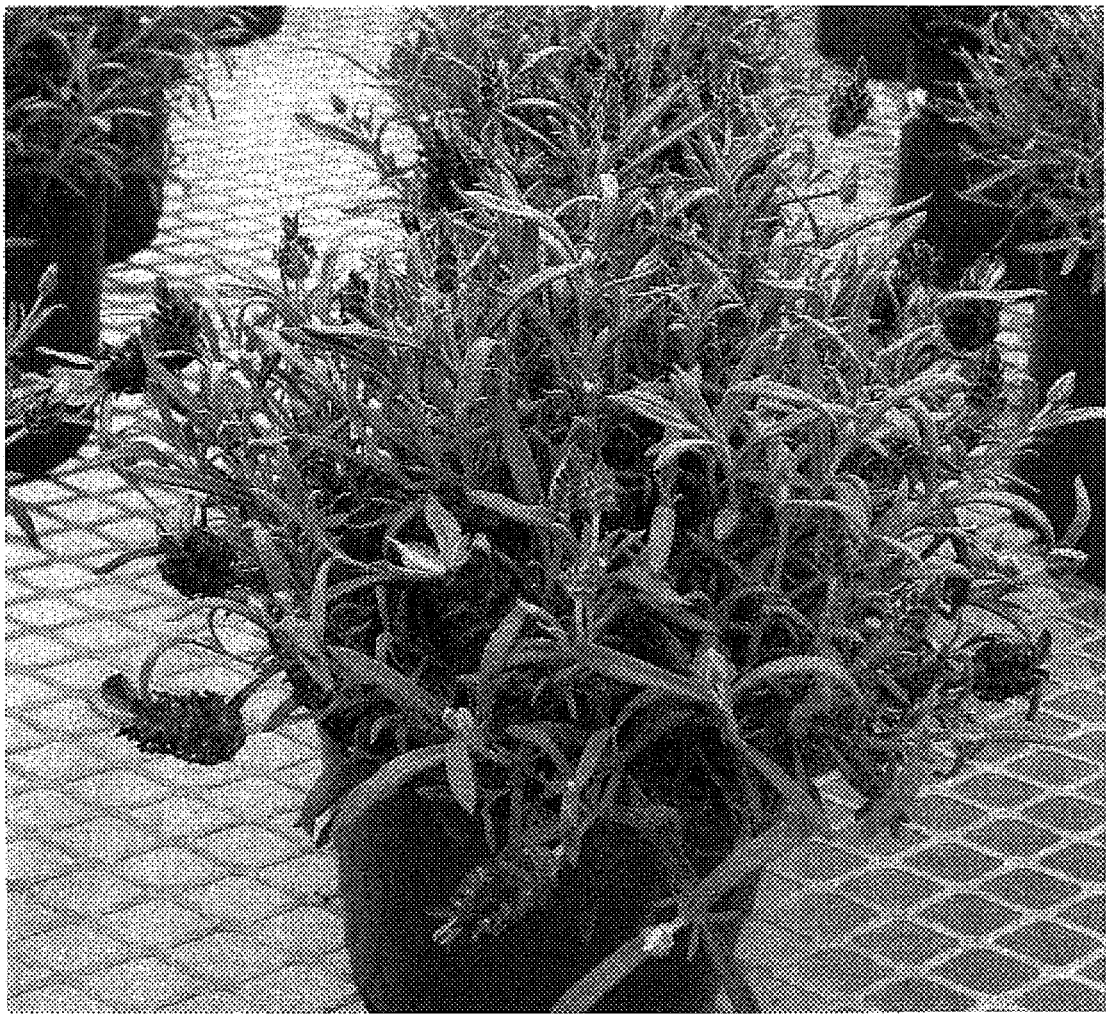
FIG. 1 depicts the plant in bloom from a side perspective. The drawing was made using conventional techniques and although the leaf and flower colors may appear different from the actual colors due to light reflectance, they are as accurate as possible by conventional photography.

The following is a detailed botanical description of the *Lavandula* cultivar named 'MULBERRY RUFFLES'. Data was collected in Arroyo Grande, Calif. from 9-month-old plants greenhouse grown in 16 cm. containers. Color determinations are made in accordance with the 2001 Royal Horticultural Society Colour Chart of London, England, except where general color terms of ordinary dictionary significance are used. The growing requirements are similar to the species.

Classification:

*Botanical classification.*—*Lavandula stoechas* 'MULBERRY RUFFLES'.
*Family.*—Lamiaceae.
*Genus.*—*LAVANDULA*.
*Species.*—*stoechas*.
*Variety denomination.*—'MULBERRY RUFFLES'.
*Common name.*—Lavender.

Plant:

*Habit.*—Dense.
*Height* (*at maturity*).—60 cm.
*Width* (*at maturity*).—70 cm.
*Life cycle.*—Perennial.
*Use.*—Ornamental for container or landscape.
*Vigour.*—Moderate.
*Hardiness.*—USDA Zone 8.
*Propagation.*—Tip and stem cuttings.
*Root system.*—Fibrous.
*Cultural requirements.*—Full sun, adequate but not excess water, and well-draining soil.
*Time to produce a rooted cutting.*—4–6 weeks.
*Time to produce a* 10 cm. container plant in bloom.—20 weeks.
*Seasonal interest.*—Flower spikes in spring and summer.
*Parentage.*—*Lavandula stoechas* 'MULBERRY RUFFLES' is a selection that resulted from controlled cross-pollination of the following parents: Female parent plant: *Lavandula stoechas* 'Kew Red'. Male parent plant: *Lavandula stoechas* 'Pukehou'.
*Disease and insect resistance.*—Minimal disease and insect susceptibility with occasional aphids on new growth.

Stem:

*Branching.*—Erect and trailing.
*Stem shape.*—Quadrangular.
*Stem surface.*—Pubescent.
*Pubescence color.*—156D.
*Stem color.*—Individual colors N199A and N144A.
*Stem length.*—Average is 10 cm.
*Stem width.*—4 mm.
*Stem fragrance.*—Resinous scent.
*Internode length.*—Range of 1 cm to 1.75 cm.

Foliage:

*Leaf arrangement.*—Whorled.
*Leaf division.*—Simple.
*Leaf shape.*—Linear.
*Leaf margin.*—Entire.
*Leaf apex.*—Acute.
*Leaf base.*—Attenuate.
*Leaf attachment.*—Sessile.
*Leaf color* (*adaxial surface*).—138A.
*Leaf color* (*abaxial surface*).—138B.
*Leaf surface* (*adaxial and abaxial surfaces*).—Pubescent.
*Color of hairs.*—156D.
*Venation.*—Reticulate.
*Vein color* (*adaxial surface*).—138A.
*Vein color* (*abaxial surface*).—138B.
*Leaf length.*—Range of 2 cm to 4 cm.
*Leaf width.*—Range of 0.25 cm. to 0.50 cm.
*Leaf fragrance.*—Resinous scent.

Inflorescence:

*Fragrance.*—Resinous scent.
*Blooming period.*—April through August.
*Inflorescence type.*—Spike.
*Spike length.*—4.50 cm.
*Spike diameter.*—1.50 cm.
*Spike shape.*—Conical.
*Spike quantity.*—Average of 35 per container plant.
*Peduncle length.*—4.25 cm.
*Peduncle width.*—1.50 mm.
*Peduncle shape.*—Quadrangular.
*Peduncle color.*—Individual colors N144A and 187A.
*Peduncle surface.*—Tomentose.
*Tomenta color.*—156D.
*Bud dimensions.*—3 mm in length and 1.50 mm in width.
*Bud shape.*—Ovoid.
*Bud color.*—N187A.
*Bud surface.*—Lanate.

*Bud apex.*—Acute.

(individual flower is referred to as corolla)

*Corolla number.*—Range of 12–15 on an individual spike.

*Corolla color.*—70A or 71A fading to N80B and N80C.

*Corolla shape.*—Salverform.

*Corolla depth.*—5 mm.

*Corolla diameter.*—3 mm.

*Corolla tube depth.*—4 mm.

*Corolla tube diameter.*—2 mm.

*Petals.*—Four in number.

*Petals fused or unfused.*—Basally fused.

*Petal shape.*—Reniform.

*Petal length.*—1 mm.

*Petal width.*—1.25 mm.

*Petal apex.*—Obtuse and emarginated petal apices individually observed on an individual corolla.

*Petal margin.*—Entire.

*Petal surface* (*adaxial and abaxial*).—Glabrous.

*Petal color* (*adaxial and abaxial surfaces*).—70A or 71A fading to N80B and N80C.

*Calyx color.*—Individual colors 187A and N144A.

*Calyx shape.*—Tubular.

*Calyx surface.*—Lanate.

*Color of hairs.*—155B.

*Calyx length.*—3 mm.

*Calyx width.*—2.10 mm.

*Sepals.*—Four in number.

*Sepals fused or unfused.*—Fused along three-quarters of the length.

*Sepal apex.*—Acute. (Fertile bract)

*Fertile bract shape.*—Deltoid.

*Quantity.*—Average of 26 per inflorescence.

*Fertile bract length.*—1 cm.

*Fertile bract width.*—1 cm.

*Fertile bract color* (*ventral and dorsal surfaces*).—Individual colors 187A and N144A.

*Vein pattern.*—Reticulate.

*Vein color* (*ventral and dorsal surfaces*).—138B.

*Fertile bract apex.*—Acute.

*Fertile bract base.*—Truncate.

*Fertile bract surfaces* (*ventral and dorsal*).—Lanate.

*Fertile bract margin.*—Entire. (Sterile bract)

*Sterile bracts.*—Average of 6 per spike.

*Arrangement.*—Whorled.

*Sterile bract appearance.*—Irridescent.

*Sterile bract form.*—Petaloid.

*Sterile bract surfaces* (*abaxial and adaxial*).—Pubescent.

*Color of hairs.*—155B.

*Sterile bract shape.*—Oblong-oblanceolate.

*Sterile bract margin.*—Entire.

*Sterile bract length.*—Range of 2 cm. to 2.50 cm.

*Sterile bract width.*—Range of 0.40 cm. to 0.75 cm.

*Sterile bract apex.*—Acute.

*Sterile bract base.*—Rounded.

*Sterile bract color* (*abaxial and adaxial surfaces*).—N80B.

*Vein pattern.*—Reticulate.

*Vein color* (*abaxial and adaxial surfaces*).—N80A.

Reproductive organs:

*Stamens.*—Four in number.

*Stamen form.*—Adnate to ventral surface of corolla tube.

*Stamen color.*—155C.

*Stamen length.*—5 mm.

*Anther.*—Four.

*Anther color.*—161A.

*Pollen color.*—161C.

*Pollen quantity.*—Moderate.

*Pistil.*—One.

*Pistil length.*—3 mm.

*Pistil color.*—155B.

*Stigma height.*—Less than 0.50 mm.

*Stigma surface.*—Glossy.

*Stigma shape.*—Orbicular.

*Stigma color.*—79A.

*Ovary dimensions.*—Less than 0.50 cm.

*Ovary shaped.*—Globose.

*Ovary color.*—138A.

*Ovary position.*—Superior.

Seed: No seed has been observed to date.

What is claimed is:

1. A new and distinct variety of *Lavandula* plant named 'MULBERRY RUFFLES' as described and illustrated herein.

* * * * *